US009469869B2

(12) United States Patent
Takayama et al.

(10) Patent No.: US 9,469,869 B2
(45) Date of Patent: Oct. 18, 2016

(54) SOLUTION MICROARRAYS AND USES THEREOF

(75) Inventors: Shuichi Takayama, Ann Arbor, MI (US); Hossein Tavana, Ann Arbor, MI (US); Andreja Jovic, Ann Arbor, MI (US); Bobak Mosadegh, Irvine, CA (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 1582 days.

(21) Appl. No.: 13/060,560

(22) PCT Filed: Aug. 4, 2009

(86) PCT No.: PCT/US2009/052632
§ 371 (c)(1),
(2), (4) Date: Apr. 13, 2011

(87) PCT Pub. No.: WO2010/027590
PCT Pub. Date: Mar. 11, 2010

(65) Prior Publication Data
US 2011/0183868 A1    Jul. 28, 2011

Related U.S. Application Data

(60) Provisional application No. 61/094,560, filed on Sep. 5, 2008.

(51) Int. Cl.
*C12Q 1/00* (2006.01)
*C12Q 1/68* (2006.01)

(52) U.S. Cl.
CPC .................................. *C12Q 1/6837* (2013.01)

(58) Field of Classification Search
None
See application file for complete search history.

(56) References Cited

U.S. PATENT DOCUMENTS

| 7,060,669 | B1 | 6/2006 | Penttila et al. |
| 7,172,905 | B2 | 2/2007 | Mrksich et al. |
| 2003/0185230 | A1 | 10/2003 | Fisher et al. |
| 2004/0052857 | A1* | 3/2004 | Keating et al. ............... 424/490 |
| 2005/0175501 | A1 | 8/2005 | Thompson et al. |
| 2006/0078908 | A1 | 4/2006 | Pitner et al. |
| 2008/0182240 | A1 | 7/2008 | Anderson et al. |
| 2009/0209735 | A1 | 8/2009 | Koo et al. |
| 2013/0317025 | A1* | 11/2013 | Ripka .................. A61K 31/519 514/234.5 |

FOREIGN PATENT DOCUMENTS

| KR | 10-2007-0031759 A | 3/2007 |
| WO | 2010027590 A2 | 3/2010 |

OTHER PUBLICATIONS

Rumiana Dimova: "Morphologies of Vesicles Loaded with Aqueous Polymer Solution." Zweijahresbericht Jul. 2008, Jun. 1, 2009, pp. 120-121.
Max Plannck Institute of Colloids and Interfaces, Report 2007-2008, Jun. 1, 2009, pp. 1-31.

(Continued)

*Primary Examiner* — Christopher M Gross
(74) *Attorney, Agent, or Firm* — Casimir Jones, S.C.; David Casimir; Tanya Arenson

(57) ABSTRACT

The present invention relates to solution microarrays. In particular, the present invention relates to an aqueous 2-phase system for solution microarrays and uses thereof. Additional embodiments are described herein.

31 Claims, 12 Drawing Sheets

(56) References Cited

OTHER PUBLICATIONS

Greson, 1980, "Cell surface energy, contact angles and phase partition. I. Lymphocytic cell lines in biphasic aqueous mixtures", Biochimica Biophysica Acta, 602: 269-280.
Hatti-Kaul, "Aqueous two-phase systems. A general overview." Mol Biotechnol. Nov. 2001;19(3):269-77.
Takayama et al., "Teaching old liquids new tricks: Aqueous two-phase systems for cell and reagent micropatterning." Abstracts of Papers American Chemical Society 2009, 237: 336.
Toshiyuki et al., "Micropatterning bacterial suspensions using aqueous two phase systems." The Analyst Jan. 1, 2010, 135(11):2848.
Merchuk JC et al., "Aqueous two-phase systems for protein separation. Studies on phase inversion." J Chromatogr B Biomed Sci Appl. Jun. 26, 1998; 711(1-2):285-93.
Bamberger et al., "The partition of sodium phosphate and sodium chloride in aqueous dextran poly(ethylene glycol) two-phase systems." Journal of Colloid and Interface Science May 1984, 99(1):187-193.
Tavana H. et al., "Polymeric aqueous biphasic systems for non-contact cell printing on cells: engineering heterocellular embryonic stem cell niches." Adv. Mater. Jun. 25, 2010; 22(24):2628-31.

\* cited by examiner

Cell viability in DMEM+5%DEX     Cell viability in DMEM+4%PEG

Figure 5
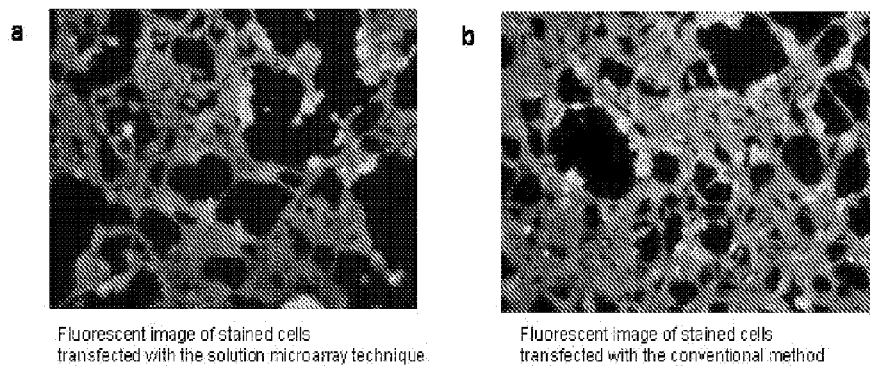
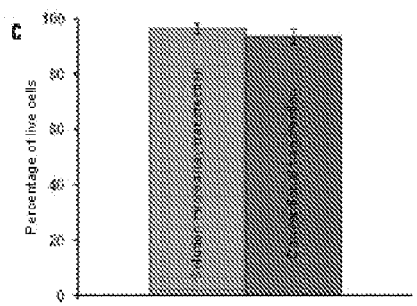
Figure 6
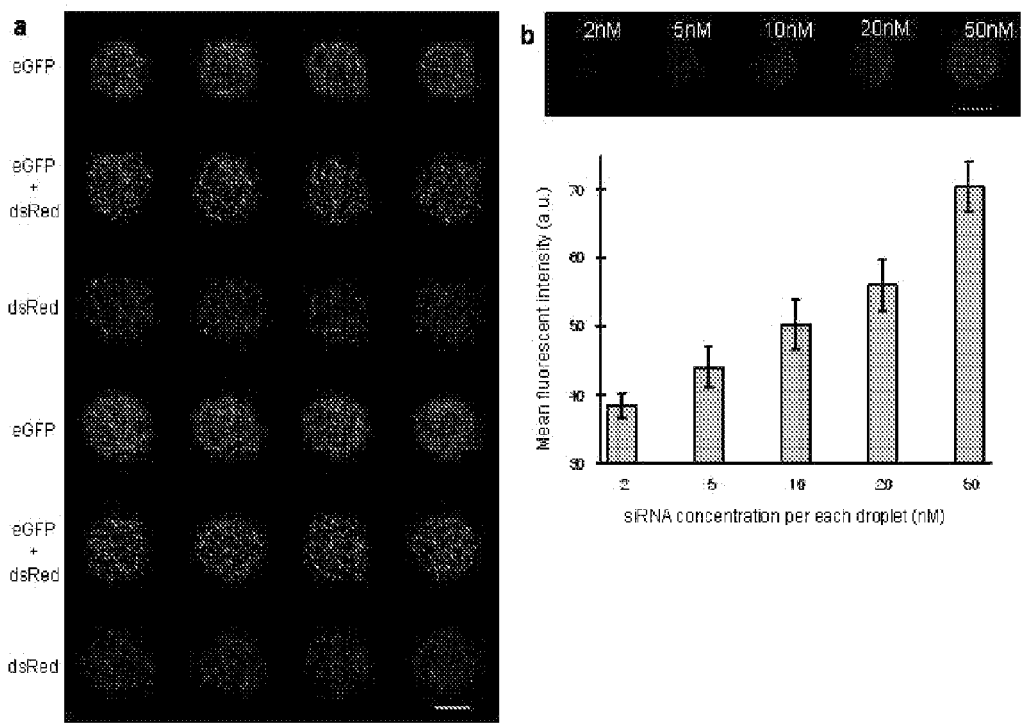

Scale bar: 1mm

Figure 18
(a)
$$-\log K = \alpha\Delta\gamma + \delta\Delta\psi + \beta \quad (1)$$
$$K = \left(\frac{C_i(top)}{C_i(bottom)}\right), \Delta\gamma = \gamma_{2c} - \gamma_{1c}, \Delta\psi = \psi_{2c} - \psi_{1c}$$
$$-\log K = \alpha\Delta\gamma + \beta \quad (2)$$
$$-\gamma_{12}\cos\theta = \gamma_{2c} - \gamma_{1c} = \Delta\gamma \quad (3)$$
$$\log K = \alpha\gamma_{12}\cos\theta + \beta \quad (4)$$
(b) 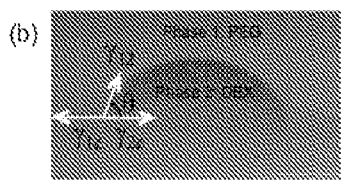
(c) 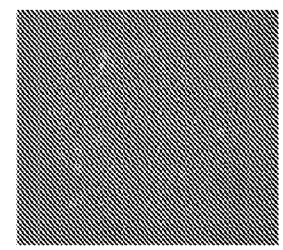
Figure 19
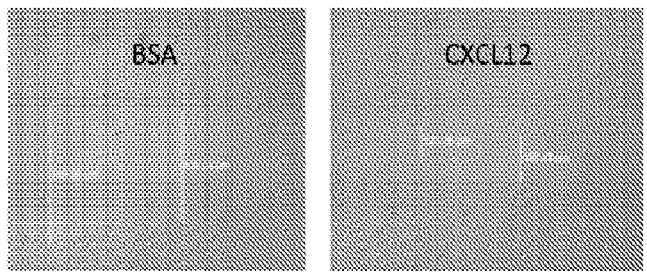
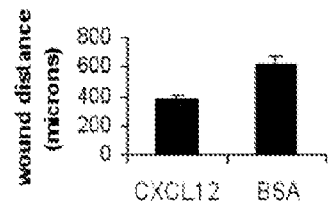
Figure 20
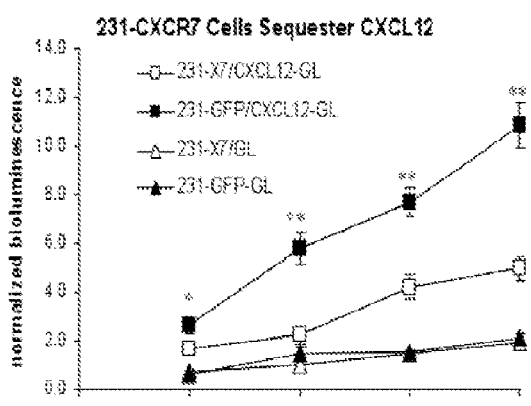
Figure 21
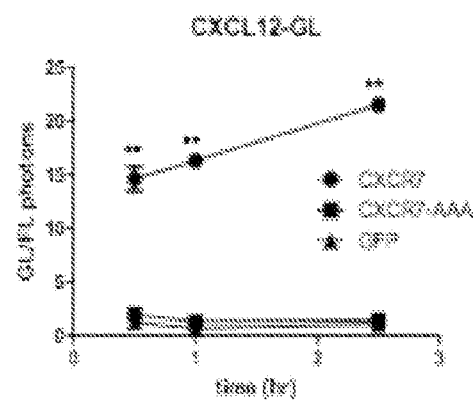

SOLUTION MICROARRAYS AND USES THEREOF

CROSS REFERENCE TO RELATED APPLICATIONS

The present application claims the benefit of priority to U.S. Provisional Patent Application Ser. No. 61/094,560, filed: Sep. 5, 2008, which is herein incorporated by reference in its entirety.

FIELD OF THE INVENTION

The present invention relates to solution microarrays. In particular, the present invention relates to an aqueous 2-phase system for solution microarrays and uses thereof.

BACKGROUND OF THE INVENTION

The identification of the entire genome sequences of many species, including humans, has set the stage for rapid advancements in the field of functional genomics. Information generated from functional analysis of genes will, in the long run, have major benefits for the prevention, diagnosis and management of many diseases which have been difficult to control. Given the large volume of data from the genome of complex organisms, functional genetic studies demand high-throughput methods to rapidly elucidate the function of many genes in parallel. Cell-based microarray systems are simple and low-cost, yet powerful tools that allow large-scale manipulation of genes in cells and analysis of corresponding downstream phenotypes. Currently, these arrays are realized by using either microwell plates that spatially segregate reagents using physical walls or solid substrates (glass or polystyrene) "printed" in certain spots with reagents suspended in a gel material. The printing method, also known as reverse transfection, offers higher density and simplified fluid handling once the reagents are printed and several groups have shown its potential for high-throughput studies of gene function. Nevertheless, this technique is inflexible in timing of delivery and removal of reagents, which limits the possibility of exposure of cells to a biochemical for a desired time period, and addition of certain components is required to stabilize transfection reagents. Most importantly, the printed gel that immobilizes reagents on the surface, by necessity, becomes the substrate to which cells attach and grow. This is a major concern for phenotypic assays since the influence of interactions between cells and their ECM on gene expression patterns of cells is ignored.

New methods are needed for cellular arrays to allow for parallel analysis of multiple genes in one assay.

SUMMARY OF THE INVENTION

The present invention relates to solution microarrays. In particular, the present invention relates to an aqueous 2-phase system for solution microarrays and uses thereof. Additional embodiments are described herein.

In some embodiments, the present invention provides a system comprising a first solution comprising a first polymer; a second solution comprising a second polymer, wherein the second solution is denser than the first solution and wherein the first and second solutions form an aqueous two-phase system when mixed; a solid support (e.g., comprising a plurality of cells affixed thereto); and, optionally, a solution comprising a plurality of cells for printing on the solid support or the aqueous two-phase system formed on the support. In some embodiments, the system further comprises genetic material (e.g., including, but not limited to, DNA, RNA, siRNA, shRNA, DNA encoding siRNA, DNA encoding shRNA, virus and phage). In some embodiments, the system further comprises a test compound (e.g., a drug). In some embodiments, the first polymer is polyethylene glycol (PEG). In some embodiments, the second polymer is dextran (DEX). In some embodiments, the first or second solutions comprise two or more polymers (e.g., DEX-methylcellulose, DEX-polyvinyl alcohol, PEG-DEX sulfate, polyvinyl alcohol-DEX sulfate, or DEX sulfate-methylcellulose). In some embodiments, the system further comprises a detection component configured for detection of altered cells (e.g., a microscope or a fluorimeter). In some embodiments, the system further comprises a cell suspension. In some embodiments, the system further comprises ultrasound contrast agents and ultrasound transducers. In some embodiments, the system further comprises cell membrane molecules and/or growth factors. In some embodiments, the system further comprises a first liposome and the second solution further comprises a second liposome, wherein the solutions are configured to a form a lipid bilayer on the support when mixed.

Embodiments of the present invention further provide a method comprising contacting a plurality of cells affixed to a solid or semi-solid support, to other cells, or to tissues with a first solution comprising a first polymer to form coated cells, contacting a portion of the coated cells with a second solution comprising a second polymer and a molecule of interest wherein the first and second solutions form an aqueous two-phase system when mixed under conditions such that the portion of the coated cells is contacted with the molecule of interest. In some embodiments, the molecule of interest is a nucleic acid (e.g., DNA, RNA, siRNA, shRNA, DNA encoding siRNA, DNA encoding shRNA) and the portion of the cells are transfected with the nucleic acid. In some embodiments, the molecule of interest is a virus or a phage. In some embodiments, the molecule of interest is a test compound (e.g., a drug), a cell, an ultrasound contrast agent, lipid molecule, growth factor or other particle. In some embodiments, the first polymer is PEG. In some embodiments, the second polymer is DEX. In some embodiments, the first or second solutions comprise two or more polymers (e.g., DEX-methylcellulose, DEX-polyvinyl alcohol, PEG-DEX sulfate, polyvinyl alcohol-DEX sulfate, or DEX sulfate-methylcellulose). In some embodiments, the method further comprises the step of detecting alterations (e.g., transfection of nucleic acids, infection with virus or phage, and alterations of cellular signaling molecules) in the portion of the cells following the contacting with the molecule of interest. In some embodiments, cells are printed on an array using the described method and the molecule of interest is a cell or a tissue.

Additional embodiments are described herein.

DESCRIPTION OF THE FIGURES

FIG. 5 shows cellular viability post transfection. a. A representative image from staining of cells transfected with the solution microarray technique. b. Fluorescent image of stained cells transfected with the conventional method. c. Quantitative comparison of cellular viability post transfection with the two techniques.

FIG. 6 shows transfection of cells with multiple genes and RNA oligonucleotides. a. Fluorescent micrograph of arrays of cells transfected with plasmid DNAs for eGFP, dsRed, or both. b. An array of HEK293H cells transfected with different concentrations of an Alexa fluor-labeled RNA duplex.

FIG. 18 shows (a) Equations describing cell partition in ATPS, (b) a droplet of DEX phase on a monolayer of 231 cells immersed in PEG phase and the interfacial tensions force balance, (c) a printed spot of C2C12 cells with optimized cell printing ATPS formulation.

FIG. 19 shows CXCL12-mediated cell migration.

FIG. 20 shows that CXCR7 cells sequester CXCL12 in coculture.

FIG. 21 shows that mutant CXCR7-AAA does not accumulate chemokine ligands.

Figure 22:
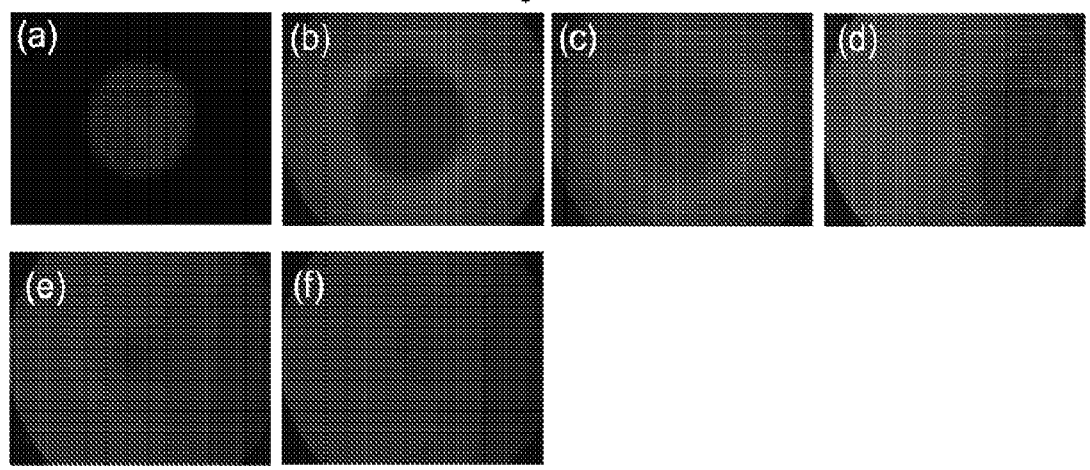

FIG. 22 shows the utility of the two-phase system to form printed lipid bilayers. a. Spot of printed lipid bilayer obtained using a 1 μl droplet of POPC liposome suspended in the DEX phase and dispensed into a bath of Hydroxypropyldextran. b,c. Polymer solutions were washed away and a second liposome was added resulting in a colored bilayer surrounding the bilayer spot. d. 60× magnification of the interface between different colored bilayers. e,f. Printed lipid bilayers are completely fluid and recover after photobleaching.

DEFINITIONS

To facilitate an understanding of the present invention, a number of terms and phrases are defined below:

The term "sample" in the present specification and claims is used in its broadest sense. On the one hand it is meant to include a specimen or culture. On the other hand, it is meant to include both biological and environmental samples. A sample may include a specimen of synthetic origin.

Biological samples may be animal, including human, fluid, solid (e.g., stool) or tissue, as well as liquid and solid food and feed products and ingredients such as dairy items, vegetables, meat and meat by-products, and waste. Biological samples may be obtained from all of the various families of domestic animals, as well as feral or wild animals, including, but not limited to, such animals as ungulates, bear, fish, lagamorphs, rodents, etc.

Environmental samples include environmental material such as surface matter, soil, water and industrial samples, as well as samples obtained from food and dairy processing instruments, apparatus, equipment, utensils, disposable and non-disposable items. These examples are not to be construed as limiting the sample types applicable to the present invention.

As used herein, the term "cell" refers to any eukaryotic or prokaryotic cell (e.g., bacterial cells such as E. coli, yeast cells, mammalian cells, avian cells, amphibian cells, plant cells, fish cells, and insect cells), whether located in vitro or in vivo.

As used herein, the term "cell culture" refers to any in vitro culture of cells. Included within this term are continuous cell lines (e.g., with an immortal phenotype), primary cell cultures, transformed cell lines, finite cell lines (e.g., non-transformed cells), and any other cell population maintained in vitro.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

As used herein, the term "selectable marker" refers to the use of a gene that encodes an enzymatic activity that confers the ability to grow in medium lacking what would otherwise be an essential nutrient (e.g. the HIS3 gene in yeast cells); in addition, a selectable marker may confer resistance to an antibiotic or drug upon the cell in which the selectable marker is expressed. Selectable markers may be "dominant"; a dominant selectable marker encodes an enzymatic activity that can be detected in any eukaryotic cell line. Examples of dominant selectable markers include the bacterial aminoglycoside 3' phosphotransferase gene (also referred to as the neo gene) that confers resistance to the drug G418 in mammalian cells, the bacterial hygromycin G phosphotransferase (hyg) gene that confers resistance to the antibiotic hygromycin and the bacterial xanthine-guanine phosphoribosyl transferase gene (also referred to as the gpt gene) that confers the ability to grow in the presence of mycophenolic acid. Other selectable markers are not dominant in that their use must be in conjunction with a cell line that lacks the relevant enzyme activity. Examples of non-dominant selectable markers include the thymidine kinase (tk) gene that is used in conjunction with tk– cell lines, the CAD gene that is used in conjunction with CAD-deficient cells and the mammalian hypoxanthine-guanine phosphoribosyl transferase (hprt) gene that is used in conjunction with hprt– cell lines. A review of the use of selectable markers in mammalian cell lines is provided in Sambrook, J. et al., Molecular Cloning: A Laboratory Manual, 2nd ed., Cold Spring Harbor Laboratory Press, New York (1989) pp. 16.9-16.15.

As used, the term "eukaryote" refers to organisms distinguishable from "prokaryotes." It is intended that the term encompass all organisms with cells that exhibit the usual characteristics of eukaryotes, such as the presence of a true nucleus bounded by a nuclear membrane, within which lie the chromosomes, the presence of membrane-bound organelles, and other characteristics commonly observed in eukaryotic organisms. Thus, the term includes, but is not limited to such organisms as fungi, protozoa, and animals (e.g., humans).

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

The terms "test compound" and "candidate compound" refer to any chemical entity, pharmaceutical, drug, and the like that is a candidate for use to treat or prevent a disease, illness, sickness, or disorder of bodily function. Test compounds comprise both known and potential therapeutic compounds. A test compound can be determined to be therapeutic by screening using the screening methods of the present invention. In some embodiments of the present invention, test compounds include antisense, siRNA or shRNA compounds.

As used herein, the term "processor" refers to a device that performs a set of steps according to a program (e.g., a digital computer). Processors, for example, include Central Processing Units ("CPUs"), electronic devices, or systems for receiving, transmitting, storing and/or manipulating data under programmed control.

As used herein, the term "memory device," or "computer memory" refers to any data storage device that is readable by a computer, including, but not limited to, random access memory, hard disks, magnetic (floppy) disks, compact discs, DVDs, magnetic tape, flash memory, and the like.

DETAILED DESCRIPTION OF THE INVENTION

The present invention relates to solution microarrays. In particular, the present invention relates to an aqueous 2-phase system for solution microarrays and uses thereof. In some embodiments, the present invention provides compositions and methods for addressing cells and reagents to one of the multiple phases of an aqueous multi phase cell culture system. In some embodiments, the system and methods are used to deliver reagents (e.g., nucleic acids in a transfection complex or viruses) to arrays of cells. The solution based arrays allow for precise and accurate delivery of reagents to only those locations desired and not to others. Although the compositions and methods described herein are illustrated with the use of printing on cells, the present invention is not limited to printing on cells. The "cell" surface may be replaced by surfaces other than cells and work in a similar manner.

I. Microarrays

Figure 1:
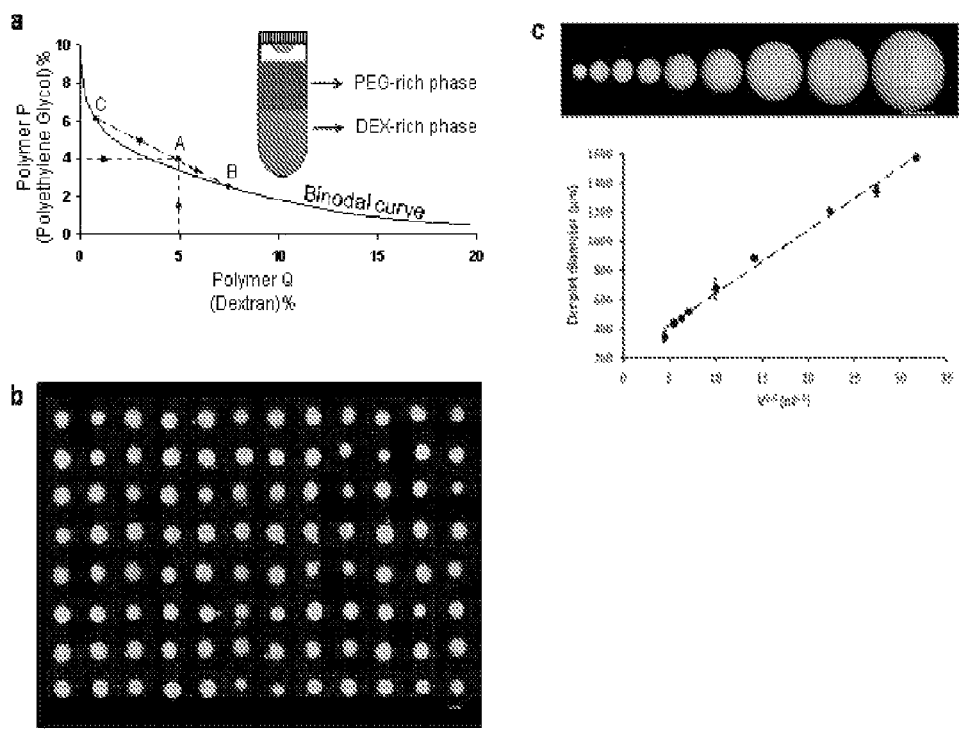
FIG. 1 shows an aqueous two-phase system (ATPS) comprising Polyethylene glycol (PEG) and Dextran (DEX) as phase forming polymers. a. Phase diagram of an ATPS describing the composition of each phase and the range of concentrations that results in phase separation. b. A 12×8 microarray of FITC-DEX aqueous solution was formed in PEG solution using 500 nl dispensing slot pins resting on a 1536-well plate format fixture. c. The size of the DEX droplet varies linearly with the square root of the volume of the dispensed DEX solution.

In some embodiments, the present invention provides multi (e.g., 2) phase solution based microarrays. The present invention is not limited to particular components of the microarray. In some embodiments, the components are aqueous polymers. Preferred polymers are those that form an aqueous two phase system (ATPS) at a wide range of temperatures (See FIG. 1 for an illustration of a phase diagram for an exemplary ATPS). Any system that selectively partitions larger molecules (e.g., cells) or smaller molecules (e.g., nucleic acids or viruses) may be utilized. Examples of suitable polymers include, but are not limited to, polyethylene glycol (PEG), dextran (DEX), and combinations of other polymers such as DEX-methylcellulose, DEX-polyvinyl alcohol, PEG-DEX sulfate, polyvinyl alcohol-DEX sulfate, hydroxypropyldextran-DEX, and DEX sulfate-methylcellulose.

In other embodiments, ATPS that exhibit variable phase separation with temperature are utilized. In some embodiments, such systems utilize low molecular weight polymers.

In some embodiments, the first layer (e.g., PEG containing media) is dispensed onto cells (e.g., a confluent layer of cultured cells). In some embodiments, genetic material to be transferred to the array is placed in the wells of a multi well (e.g., 1536 well) plate. In some embodiments, the molecule of interest (e.g., genetic material) is in a solution containing the second component of the ATPS (e.g., Dex). In some embodiments, a transport component (e.g., an array of slot pins) is then used to transfer the molecule of interest onto the cell array. For example, in some embodiments, a multiplex dispenser that allows different materials to be added to different spots on the array is utilized. In some embodiments, the dispenser is a plurality of pins or other dispensing components affixed to a single transport component. In some embodiments, the transport component is automated.

In some embodiments, the component comprising the molecule of interest is denser that the first component and thus displaces the first material and contacts the cells. In some embodiments, cells are then transfected with the genetic material.

II. Uses

The solution based microarrays of the present invention find use in a variety of applications. Any application that requires manipulation of cells, reagents or surfaces in an array format is amenable to the methods of the present invention.

In some embodiments, the compositions and methods of the present invention find use in transfection methods. For example, in some embodiments, cells to be transfected are placed under the first solution. The genetic material is placed in the second solution and selectively delivered to cells. The present invention is not limited to a particular type of genetic material. Examples include, but are not limited to, DNA, virus, phage, RNA (e.g., antisense, shRNA or siRNA) or DNA encoding antisense, shRNA or siRNAs. Using such methods, it is possible to deliver multiple different types of genetic material to the same array of cells.

In some embodiments, cells are transfected using ultrasound. For example, in some embodiments, DNA is delivered to specific cells using the ATPS systems described herein and ultrasound contrast agent bubbles are used to introduce genetic material into cells via ultrasound.

In other embodiments, additional transfection systems and reagents are included (e.g., lipid based transfection systems, electroporation systems, etc.).

In other embodiments, the compositions and methods of the present invention find use in drug screening applications. For example, in some embodiments, cells to be screened (e.g., cancer or disease cells) are placed under the first solution. Candidate compounds are then placed in the second solution and selectively delivered to cells. In some embodiments, candidate compounds are therapeutic nucleic acids (e.g., siRNA, antisense or DNA encoding therapeutic RNAs). Using such methods, it is possible to deliver multiple different candidate compounds to the same array of cells.

In other embodiments, cells are contacted with additional molecules of interest including, but not limited to, cell signaling molecules (e.g., cytokines), growth factors, proteins, etc. and the effect of the molecule on the cell is assayed.

In still further embodiments, the present invention provides systems and methods for detecting cell-cell and cell-tissue interactions. For example, in some embodiments, a substrate immersed in a first solution is printed with cells suspended in a second solution, allowing localized delivery. The cellular array can then be contacted with a second cell or cell type (e.g., to study cell-cell interactions) or a tissue (e.g., for use in tissue engineering or research).

Following manipulation of cells, altered (e.g., transfected) cells may be detected using any suitable read out method. In some embodiments, the read out is an immunofluorescence method where antibodies to protein expressed from a transfected cell is contacted with the transfected array. Fluorescence is detected using any suitable method (e.g., a microscope or a fluorimeter).

In other embodiments, a different detection method including, but not limited to, fluorescence in situ hybridization, reporter assay (e.g., with fluorescence, chemical or chemiluminescence readout) or other detection method is utilized.

In some embodiments, cell based array methods and read out is performed in a high throughput manner. In some embodiments, high throughput methods are automated.

The present invention further provides systems and kits comprising the cell based solution arrays described herein. In some embodiments, systems and kits comprise cells (e.g., in a multiwell solid support), multiple solutions for forming arrays, transport components (e.g., robotics), and components for read out of signal from altered cells, including analysis software. In some embodiments, kits further comprise additional component useful, necessary, or sufficient for performing and analyzing the results of the methods described herein (e.g., including, but not limited to, buffers, nucleic acids, candidate drug compounds, etc.).

EXPERIMENTAL

The following examples are provided in order to demonstrate and further illustrate certain preferred embodiments and aspects of the present invention and are not to be construed as limiting the scope thereof.

Example 1

A. Methods

Cell Culture

The HEK293 cell line was obtained from ATCC(CRL-1573). Cells were maintained in DMEM (Gibco) supplemented with 10% FBS (Gibco) at 37° C. in a humid incubator with 5% CO2 and passaged every 3-4 days to avoid cell overgrowth. For transfection experiments, cells with a passage number between 5 and 30 were used.

Plasmids and Transfection Reagents eGFP (PT3148-5) and dsRed (6924-1) plasmid DNAs were obtained from Clonetech. Full-length MT1-MMP cDNA was prepared as described previously. Full-length MMP2 cDNA was obtained from Origene (SC117323).

Solution Microarray Formation for Gene Transfection

Solutions of 4% PEG (Mw: 8,000, Sigma, P2139) and 8% DEX (Mw: 500,000, Pharmacosmos A1S, 40030) were prepared in optimem (Gibco, 31985) and mixed together. After adding 5 mM KH2PO4 salt to adjust final ionic compositions of the phases, the mixture was shaken thoroughly and kept at 4° C. overnight to equilibrate and form a two-phase system. The two phases were then carefully separated and centrifuged at 3500 rpm for 45 min to remove counter polymers excessively dissolved in each phase. The stock solutions of PEG and DEX phases were stored in the fridge to retard microbial growth. Storage over one month did not change the performance of conditioned media.

Lipofectamine 2000 (Invitrogen, 11668-019), which is a cationic lipid, was used as the transfection reagent in all experiments. Dilutions of 2.5 µg plasmid DNA in 12.5 µl optimem and 2.5 µl lipofectamine in 12.5 µl optimem were prepared and incubated for 5 min at room temperature. The solutions were mixed and incubated for 20 min at room temperature. The resulting solution was mixed with 90 µl of DEX phase stock solution, incubated for 5 min at room temperature, and then transferred to wells of a 1536-well plate (Corning).

Prior to experiments, slot pins (V&P Scientific, FP3S500H) were mounted on a pin tool fixture (V&P Scientific, AFIX1536FP3), which itself is assembled with a micromanipulator. Pins were cleaned by dipping into a special cleaning solution (V&P Scientific, VP110), DI water, and isopropyl alcohol (IPA), as indicated by the manufacturer of the pins. The up and down movement of the pin tool system was controlled by the micromanipulator. Then, clean pins were dipped into the wells and filled with the solution containing transfection complexes. This was repeated three times to ensure proper mixing. Final retraction of the pins from the solution was done slowly to minimize residue on the outer surface of the pins. Next, pins were lowered into the close vicinity of the cell monolayer covered with the PEG-optimem and were allowed to dispense the complex containing DEX-optimem solution. After formation of droplets on cells, pins were slowly retracted and moved out of the culture dish. Thus, a microarray of transfection complexes was formed on defined spots in the cell culture system.

For viral transduction experiments, solutions of 4% (w/w) PEG and 15% (w/w) DEX were prepared separately in MDA-MB-231 culture medium. 40 µl lentiviral solution was suspended in 20 µl of the DEX solution to a final titer of $1.3 \times 10^7$ (IFU)/ml. To enhance viral infection of cells, a cationic agent, polybrene (Sigma), was added to the resulting solution at a final concentration of 10 µg/ml. Droplets of this solution were arrayed on cells as described above.

Preparation and Labeling of Collagen Substrates

Type I collagen was prepared from rat tail tendons and dissolved in 0.2% acetic acid to a final concentration of 2.7 mg/ml. To induce gelling, collagen was mixed with 10×MEM (GIBCO, 11436) and 0.34 N NaOH in an 8:1:1 ratio at 4° C. and 2 ml of this mixture was added to each chamber of a 2-well chambered slide (VWR, 62407-052). To obtain a thin film, collagen was immediately removed and the slide was left at 37° C. for 45 min to allow gelling to complete. The collagen film was then labeled with Alexa Fluor 594 (Molecular probes, A10239) for 1 h at room temperature. After removing the dye, the film was incubated three times with PBS pH 7.4 (GIBCO, 10010) at room temperature for a total of 30 min. Then, 2 ml PBS was added to each chamber and the slide was wrapped in an aluminum foil and stored at 4° C.

Immunofluorescence

Immunostaining of MT1-MMP was performed to detect protein expression in transfected HEK293 cells. After fixing in −20° C. methanol for 6 min, cells were washed three times with PBS and twice with PBS containing 5% BSA. The primary monoclonal antibody, mouse anti-human IgG (Covance, MMS-101P), was diluted 1:1000 in PBS/5% BSA to a concentration of 1 µg/ml and gently added to fixed cells. After incubating for 1 h, cells were washed three times with PBS and twice with PBS/5% BSA. The secondary antibody, goat anti-mouse IgG (Molecular Probes, A-11001), was diluted 1:2000 in PBS/5% BSA to a concentration of 1 µg/ml and added to cells. Cells were incubated for 1 h and washed three times with PBS.

Imaging and Fluorescence Microscopy

Transfected microarrays were imaged section by section using a conventional fluorescence microscope (Nikon, TE300). After removing the background intensity of images and performing automatic image enhancement in Matlab R2007a (MathWorks), images were pseudocolored, merged, and superimposed in Photoshop 10.0 CS3 (Adobe). SimplePCI (Compix) was used for fluorescence intensity measurements.

B. Results

Figure 2:
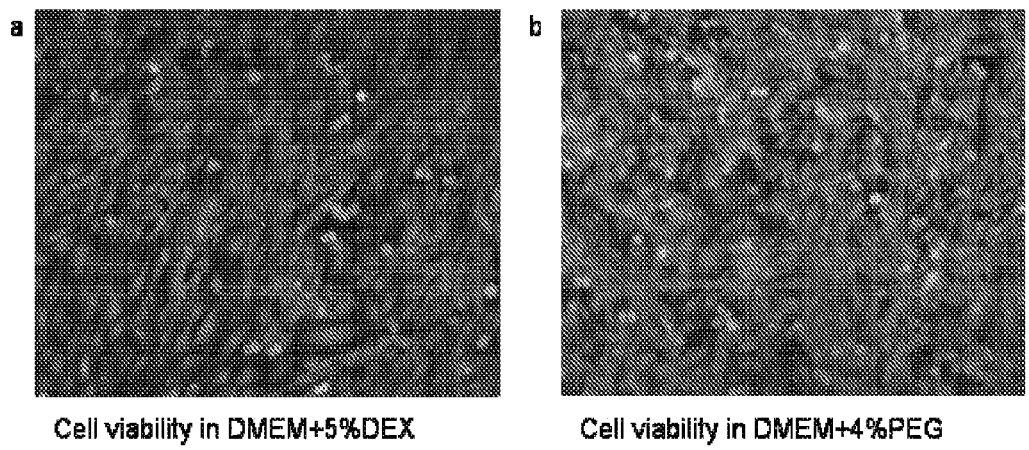
FIG. 2 shows cellular viability in reformulated culture media. a. A representative image of stained cells cultured in DMEM+5% DEX. b. A representative fluorescent image of stained cells cultured in DMEM+4% PEG.

Mixtures of aqueous solutions of various polymers, such as polyethylene glycol (PEG) and dextran (DEX), above certain concentrations phase-separate and form an ATPS (FIG. 1a). ATPSs are often used as bioseparation tools for fractionation of cells into subpopulations, purification and isolation of membrane proteins, and isolation of DNA. Separation of biomolecules is realized through their affinity partitioning to one of the two phases. This example describes an ATPS-based technology to selectively deliver genetic material into discrete groups of cells in culture. High molecular weight PEG and DEX were selected as the phase forming polymers for three main reasons. First, these polymers form ATPSs in a wide range of temperatures. This is useful because the equilibration stage of the two-phase system, which usually requires several hours, should be carried out at low temperatures whereas the components of the two-phase system should still segregate at relatively high temperatures required for the maintenance of cells. Second, due to difference in the density of the aqueous solutions of these two polymers, DEX always forms the bottom phase and PEG the top phase of the two-phase system (FIG. 1a). By dispensing small amounts of the DEX phase into a cell culture plate partially filled with the PEG phase, small DEX droplets forms at defined locations of the plate. This enables specifically targeting only those cells that rest underneath the droplet by reagents confined to the DEX phase. A microarray of 96 droplets of FITC-labeled aqueous solution of DEX in a lawn of PEG solution was formed (FIG. 1b). Fluorescent spots are about 850 µm in diameter with a center-to-center spacing of 2.25 mm. Different droplet sizes can be realized by changing the dispensing volume of the DEX phase (FIG. 1c). Third, selecting high molecular weight polymers ensures formation of the two-phase system at very low polymer concentrations so that the bulks of both phases remain highly aqueous and gentle to cells. The compatibility of these polymers with cell culture was confirmed by growing cells in media containing working concentrations of PEG and DEX. Cells in the reformulated culture media showed a viability of above 96% (FIG. 2).

Figure 3:
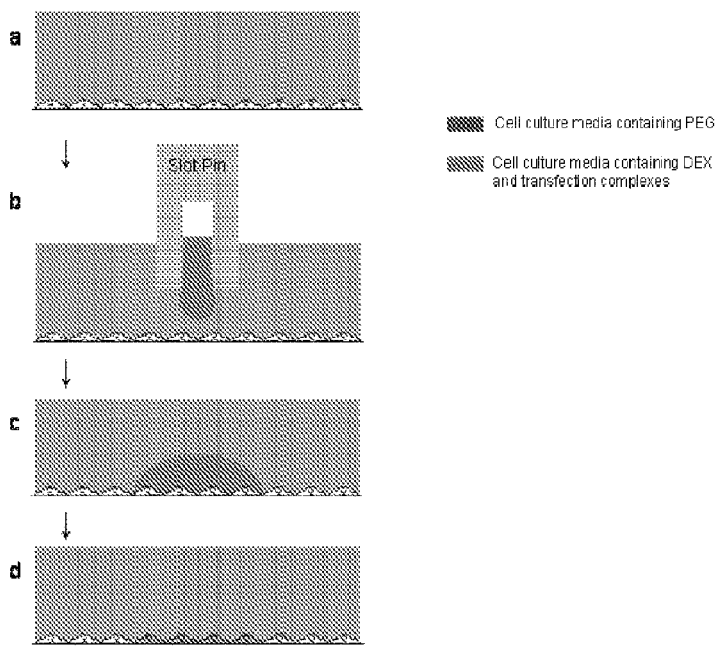
FIG. 3 shows a schematic of selective delivery of nucleic acids to cells in culture using a solution microarray system of embodiments of the present invention. a. Cells are cultured to desired confluence and prior to the experiment, they are covered with a PEG-containing culture medium. b. The slot pins resting on a fixture are filled with transfection complexes suspended in a DEX-containing culture medium and are slowly lowered into this solution using a micromanipulator that controls the vertical motion of the fixture. c. Small droplets containing transfection complexes are formed on discrete groups of cells. d. Incubating the culture system causes only those cells confined to the droplets to become transfected and exhibit the corresponding phenotype.

To form a microarray of transfected cells, a PEG-DEX two-phase system was prepared with a cell culture medium as the solvent. The top and bottom phases were carefully separated after equilibrium was reached. Then complexes of nucleic acids were prepared, mixed with the DEX phase, and transferred into the wells of a 1536-well plate. Then, an array of slot pins resting on a commercially-available fixture was dipped into this solution. This caused the pins to fill due to capillary action. The pins were then lowered to the close proximity of the cell monolayer that was already covered by the PEG phase (FIG. 3a,b). The denser DEX phase containing genetic material dispensed and formed droplets on discrete groups of cells and pins fill with the PEG phase (FIG. 3c). Then pins were refracted from the culture system. Incubating cells yields a phenotype of interest only within the targeted cells (FIG. 3d). Transfection reagents can be removed at any desired time point.

Figure 4:
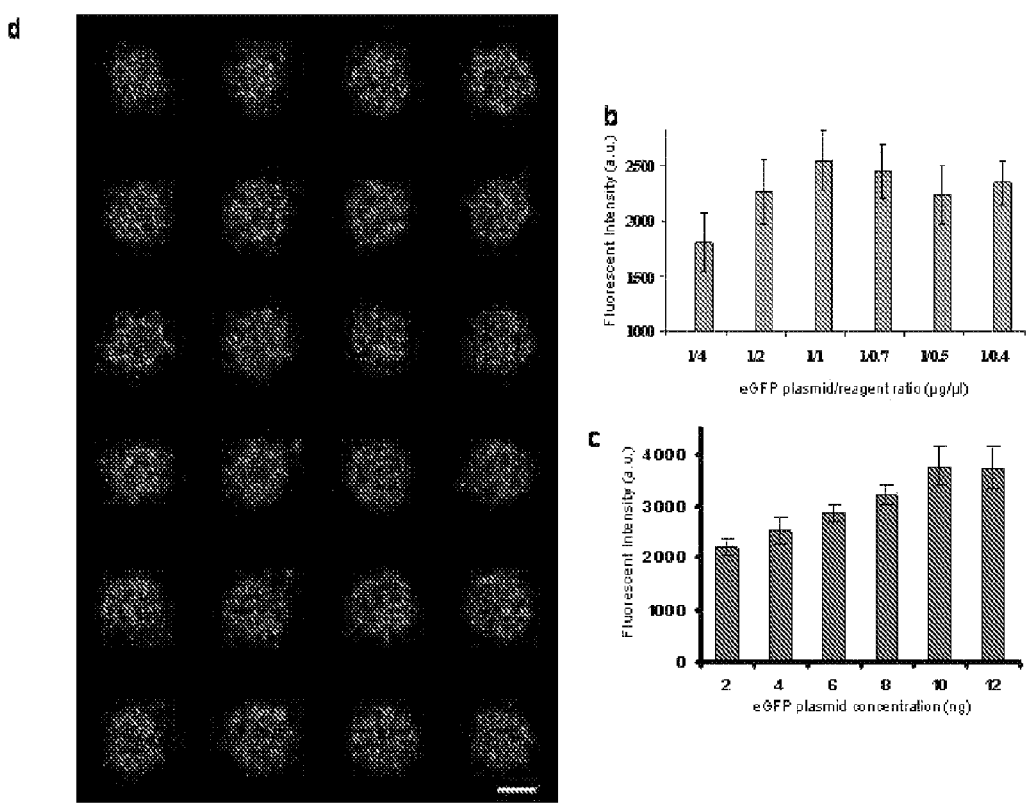
FIG. 4 shows microarrays of transfected cells using the solution microarray technology of embodiments of the present invention. a. A 6×4 microarray of HEK293 cells expressing the eGFP protein. b. The highest fluorescence intensity in the cell clusters of the microarray is obtained with a 1/1 (ng/μl) ratio of plasmid DNA/transfection reagent. c. The level of protein expression in the microarray of transfected cells initially increases with the amount of transfected plasmid DNA and then levels off.

The efficacy of the method was examined by delivering an expression construct for enhanced green fluorescent protein (eGFP) into discrete groups of HEK293 cells grown in a Petri dish. Imaging cells with a fluorescence microscope 48 hrs post transfection yielded a microarray of 24 spatially distinct cell clusters expressing eGFP in a lawn of non-transfected cells (FIG. 4a). Each cell cluster was exposed to a droplet containing only ~8 ng plasmid. The number of treated cells and the amount of plasmid can further be reduced by choosing dispensing pins with smaller volumes. By testing different ratios of plasmid DNA to the transfection reagent, it was found that optimum cell signaling is obtained with a ratio of 1/1 (FIG. 4b). The level of protein expression at various concentrations of plasmid DNA was also examined. Similar to the conventional transfection technique, fluorescent signal intensity proportionally increases with the concentration of the plasmid up to a certain point and further increase in the amount of DNA plasmid does not enhance the protein expression level (FIG. 4c). Moreover, cellular viability post transfection with solution microarray technique was assessed and compared with corresponding data from the conventional method. Cellular viability was about 95% in both cases, indicating that presence of PEG and DEX in the media does not cause cytotoxicity in the course of the transfection process (FIG. 5).

Next, the utility of the solution microarray approach to perform several transfection conditions in a single experiment was demonstrated. Transfection of HEK293 cells with plasmid DNAs for eGFP and dsRed resulted in spatially distinct groups of cells fluorescing green and red, respectively (FIG. 6a). Cells that co-express eGFP and dsRed proteins (FIG. 6a) were generated.

The technology also allows effective delivery of RNA oligonucleotides for RNA interference (RNAi) assays. RNAi is a post-transcriptional gene silencing process mediated by processed small interference RNAs (siRNAs) that target mRNAs in a sequence-specific manner and cleave them, preventing the occurrence of the translation stage. An Alexa fluor-labeled RNA duplex that possesses similar length, charge, and configuration to siRNAs was transfected at various concentrations ranging from 2 nM to 50 nM into HEK293H cells. Imaging cells 24 hrs post-transfection showed that the fluorescent signal is retained within the transfected cell clusters only and that signal intensity increases proportionally with the RNA concentration in the DEX phase droplets (FIG. 6b).

In vivo, the behavior of a cell and its response to a range of external stimuli is largely determined by its local microenvironment. The ECM is a key component of cellular microenvironment and a major regulator of gene expression patterns of a cell. Therefore, gain- and loss-of-function genetic screens in mammalian cells cultured on physiologic substrates such as the ECM proteins, rather than solid substrates, more closely reveals physiologic phenotypes associated with the expression/suppression of a protein or a group of proteins. To establish the utility of the solution micrarray technique for assays requiring soft substrates, patterned degradation of collagen I by cells expressing membrane-type1 matrix metalloproteinase (MT1-MMP) was demonstrated. Degradation of collagen is important for the physiological remodeling of connective tissue during growth and development as well as in the metastasis of cancers where malignant cells cleave their subjacent matrix proteins and initiate invasiveness. Recent findings highlight MT1-MMP as the major regulator of the collagenolytic activity of normal and neoplastic cells. HEK293 cells were cultured on Alexa fluor-labeled collagen I substrates and selectively transfected with full-length MT1-MMP cDNA. Imaging 72 hrs post-transfection showed phagocytosis of collagen I only by the transfected cells whereas the matrix remained intact elsewhere (FIG. 7a, b). The loss of collagen appears as black pits under the fluorescent light. Immunostaining of cells shows that degradation of the matrix correlates well with the expression of MT1-MMP protein (FIG. 7c). To demonstrate the specificity of MT1-MMP-induced loss of collagen, cells in the same assay were also transfected with matrix metalloproteinase 2 (MMP2) cDNA and eGFP plasmid DNA as a control. MMP-2 expressing cells lacked the invasive phenotype and were not capable of degrading the matrix (FIG. 7a,b).

Figure 8:
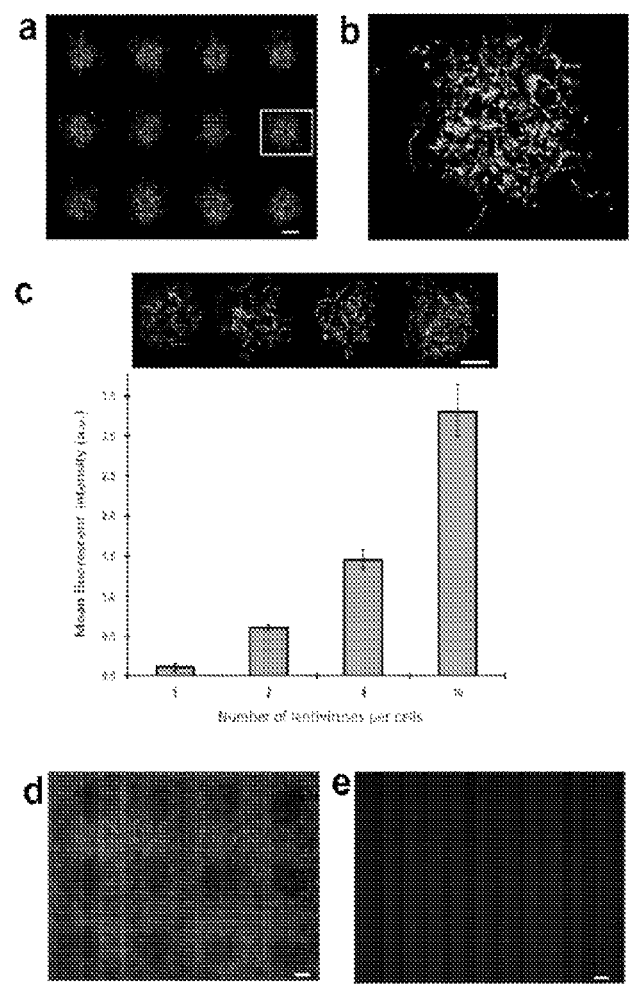
FIG. 8 shows patterned microarrays of lentiviral-mediated gene expression and gene knockdown. (a) Fluorescent image of a 3×4 array of MDA-MB-231 human breast cancer cells transduced with a lentiviral vector containing eGFP gene. (b) A magnified view of the boxed spot in (a). (c) Dose-dependent infection of cells with lentiviral vectors. (d) A 3×4 microarray of localized eGFP gene knockdown obtained with patterned infection of cells with lentiviruses encoding eGFP shRNA. (e) Cells in the spots express similar levels of the mPlum gene compared to cells outside the spots.

Lipid-mediated transfection is a straightforward method to induce transient effects of gene overexpression/knockdown in cells. However, many cell lines and primary cells do not transfect efficiently with lipofection and require infection with viral vectors containing cDNA- or short hairpin RNA (shRNA)-expressing cassettes. It was shown that the two-phase patterning approach facilitates lentiviral-mediated transduction of MDA-MB-231 human breast cancer cells. Virus particles encoding eGFP remained confined to patterned DEX droplets and resulted in the localized infection of subpopulations of cells (FIG. 8a,b). The titer of the lentiviral solution in the DEX phase was 1.3×107 infectious units (IFU)/ml that corresponded to 10 viral particles per cell.

Serial dilutions of the eGFP-encoding lentivirus were prepared and arrayed on the MDAMB-231 cells at 4, 2, and 1 viral particles per each cell. Subsequent analysis of fluorescent intensity of infected cells showed that similar to conventional well-based lentiviral infections, the level of eGFP expression increases proportionally with the amount of lentivirus in the patterned DEX phase (FIG. 8c). The lentiviral solution titer for efficient two-phase patterned infection of cells is 2-3 orders of magnitude less than that required with the reverse transfection approach where the virus are printed onto a solid substrate and subsequently overlaid with cells.

This is a major advantage that significantly reduces toxicity to cells and eliminates the need for hard-to-obtain highly concentrated viral solutions.

The utility of the two-phase patterning for lentiviral-mediated RNA interference (RNAi) was demonstrated. MDA-MB-231 cells permanently expressing CXCR4-eGFP (target gene) and mPlum (red reporter gene) constructs were seeded at a density of 37500 cells/cm². The lentivirus encoding shRNAs that specifically target eGFP mRNA were resuspended in the DEX phase and patterned on the cells. Analysis of cells 72 hrs post-infection showed a significant reduction in eGFP expression levels only within targeted cell clusters (FIG. 8d). The fact that cells within the spots actively express the reporter red protein ensures the specificity of the shRNA for the target gene (FIG. 8e).

To obtain measurable cellular phenotypes with the solution microarray technology, several technical problems were resolved. First, the composition and concentration of the phase forming polymers were optimized to retain a cellular viability comparable to that obtained with regular culture media. Second, the ionic composition of the two-phase culture media was adjusted by adding a small amount of the monopotassium phosphate salt to confine complexes of nucleic acids to the DEX-phase and prevent their spreading from the area covered by the DEX droplets. Third, establishing optimum doses of DNA as well as the ratio of DNA to the cationic lipid transfection agent ensured acceptable quantitative levels of cellular phenotypes while eliminating transfection-induced cytotoxicity to cells.

This Example describes a solution microarray technology that facilitates high-throughput functional genetic studies in mammalian cells. The method is easy to implement and economically sound requiring only off-the-shelf pin tool systems and a set of inexpensive dispensing pins to operate. It is therefore readily accessible to any laboratory without complicated equipment. In addition, it allows phenotypic screening of genetic perturbation in cells cultured on substrates such as soft gels that have not been demonstrated with previous high-throughput techniques. This unique feature generates new opportunities for various areas of research including cancer metastasis where identification of oncogenes responsible for the migration of cancer cells from the sites of primary tumors through degradation of the ECM proteins is concerned. The technology is compatible with existing standard high-throughput 96, 384, and 1536 formats. It is applicable to the functional analysis of many genes in parallel and to genome-scale screens.

Example 2

This Example describes lentivirus mediated transfection using the methods described in Example 1. Hek cells were transfected with a lentivirus containing a GFP reporter construct using a DEX-PEG system. The results indicated that selective transfection was obtained.

Example 3

Figure 9:
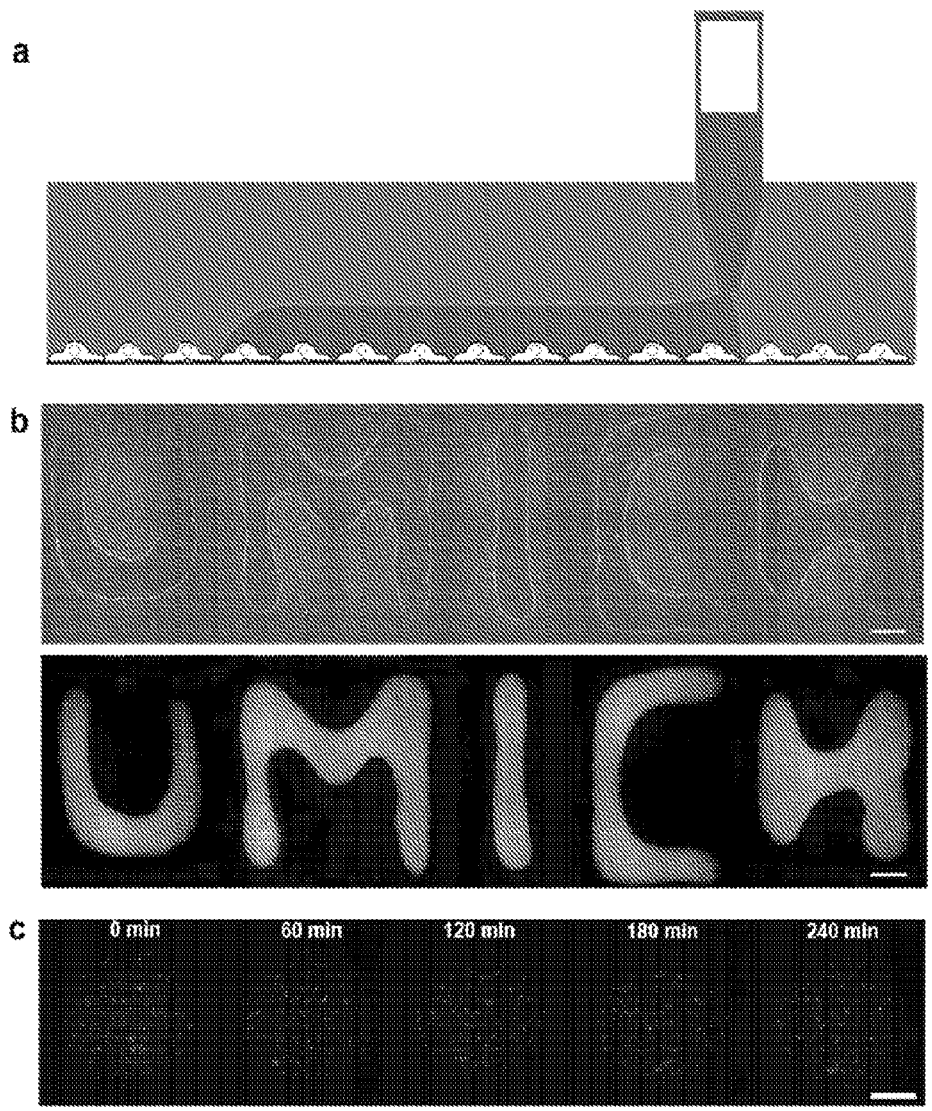
FIG. 9 shows that polymeric aqueous two-phase systems generate user-defined patterns of a reagent on a cell monolayer. (a) Schematic representation of patterning aqueous DEX phase on a cell monolayer covered with the PEG phase. (b) Bright-field and fluorescent images of patterned DEX phase on HEK293H cells spelling "UMICH". (c) Complexes of genetic materials and the transfection reagent, Lipofectamine 2000, partition well to the DEX phase and remain within the dispensed drop over a 4 hrs imaging period.
Figure 10:
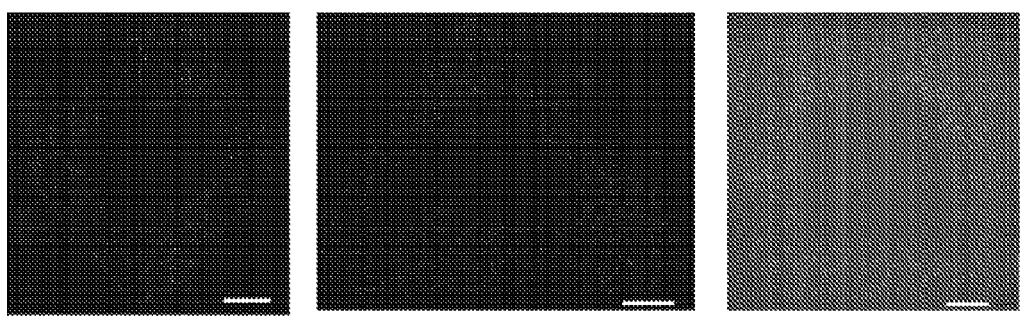
FIG. 10 shows long term stability of patterned genetic reagents on cells. Complexes of a transfection reagent, Lipofectamine 2000, and dsRed or eGFP genes were mixed with the DEX phase and patterned in different shapes of diamond, triangle, and square on HEK293H immersed in the PEG phase and incubated at 37° C. and 95% humidity for 8 hrs. 48 hrs post incubation at regular culture media, cells showed localized expression patterns of dsRed and eGFP genes that exactly mimic the shapes of printed reagents.
Figure 11:
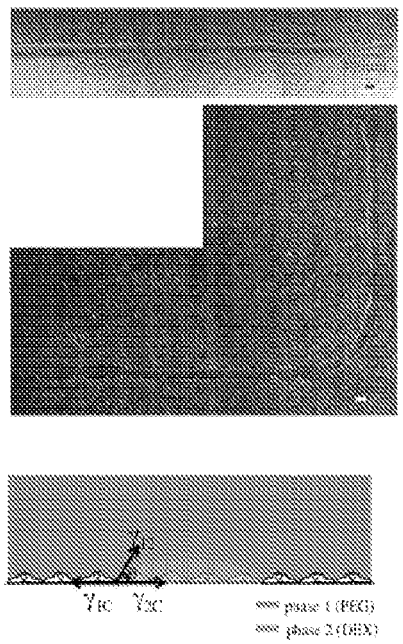
FIG. 11 shows design principles regarding the resolution of arbitrarily shaped patterns. The resolution of arbitrary patterns can be enhanced by reducing the size of the dispensing tip used.

Methods are as described in Example 1 above. To generate user-defined shapes of the reagent phase, a pipette tip is loaded with the DEX phase and lowered into the PEG phase in close proximity (typically <500 μm) to the cell monolayer. Moving the pipette tip horizontally results in the formation of a continuous pattern of the dispensing DEX phase on cells (FIG. 9a). This is demonstrated by patterning "UMICH" on a monolayer of HEK293H cells (FIG. 9b). The resolution of patterns can be improved by using dispensing mechanisms with finer tips (FIG. 11). Other shapes, such as triangles and squares, can also be created (FIG. 10); the patterns are quite stable over long incubation time periods and are not disturbed by carefully moving the cell culture system.

Figure 12:
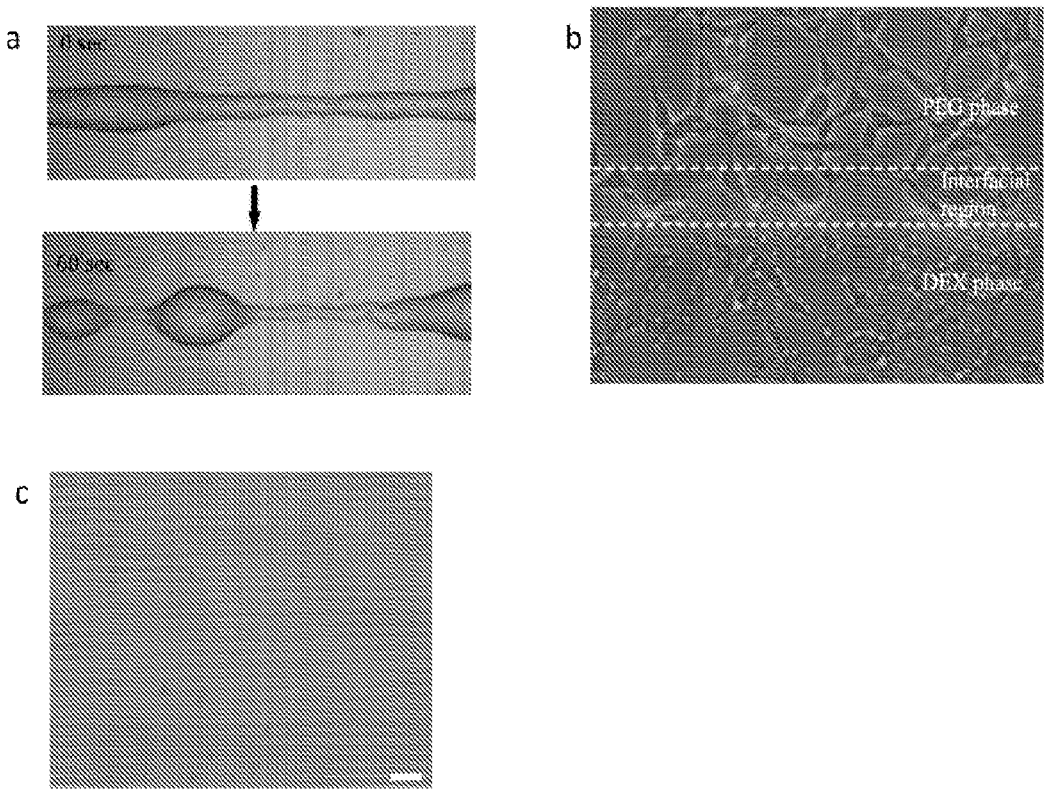
FIG. 12 shows stability of printed patterns. (a) To pin down the effect of low $\gamma_{12}$ on pattern stability, a twophase system with higher concentrations of polymers, i.e. 7% PEG/12% DEX was used. (b) The surface of cells possesses a rough structure of a few microns (c) As a negative control to show lack of stability of patterns on a surface with nanometer scale roughness, a surface was fabricated with nanometer roughness obtained by molding polydimethyl siloxane (PDMS) against a silicon nanostamp (LightSmyth Technologies). Patterns were not stable on this nanomater scale rough surface.

The key to the stability of patterns is an extremely low interfacial energy between the two immiscible phases ($\gamma_{12}$~0.003 mJ/m²) and roughness of the cell monolayer surface and associated cell-surface-DEX phase interactions (FIG. 12). Thermodynamically speaking, cell monolayer surface gives rise to free energy barriers that prevent the PEG-DEX interfacial tension, $\gamma_{12}$, from retracting the three-phase contact line (PEG-DEX-cell surface) of the patterns to a lower energetic state, and thus, patterns retain their shapes.

This example describes the use of this patterning technology for microarray format multiplexed cell based studies of gene expression and gene silencing. First, partitioning of cell transfection materials in the PEG-DEX ATPS was performed. Complexes of a lipid transfection reagent, Lipofectamine 2000, and 50 nM Alexa fluor-labeled RNA were prepared and suspended in the DEX phase. A droplet of this solution was dispensed into a bath of the PEG phase and imaged every 15 min. The results show that over a period of 4 hrs, the fluorescent signal from transfection materials remains quite confined to the DEX droplet (FIG. 9c).

Figure 13:
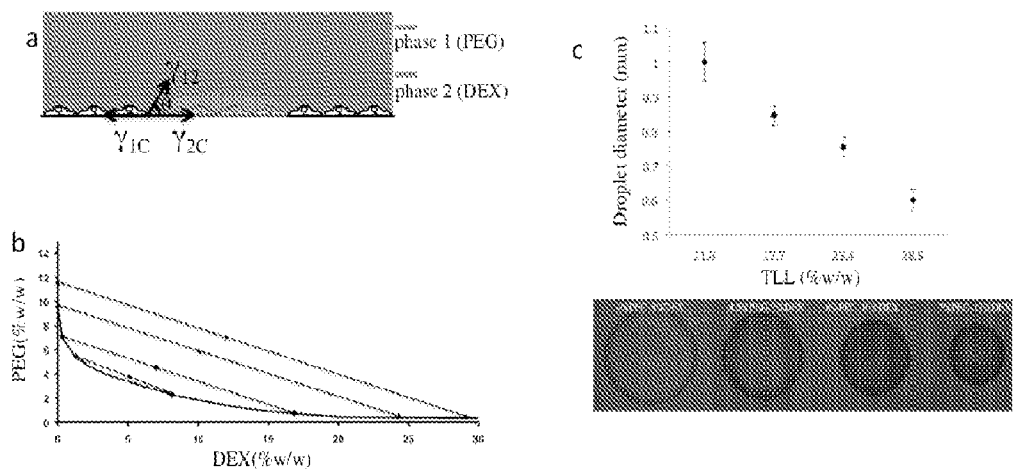
FIG. 13 shows design principles regarding the resolution of circular patterns. (a) For a given volume of dispensed liquid, the shape of DEX droplets is determined by the balance between the three interfacial tension forces: Interfacial tension between the two immiscible polymer phases, $\gamma_{12}$, and interfacial tension of each aqueous polymer phase and the cell monolayer, $\gamma_{1C}$ and $\gamma_{2C}$, respectively. (b) The interfacial tension between two immiscible aqueous polymer phases $\gamma_{12}$) directly correlates with the tie line length (TLL) through the PEG (% w/w) following empirical relation: $\text{Log}(\gamma_{12})=A+B \text{ Log}(TLL)$. (c) For a given DEX droplet volume, droplet diameter decreases consistently with increasing TLL and hence with increasing $\gamma_{12}$.
Figure 14:
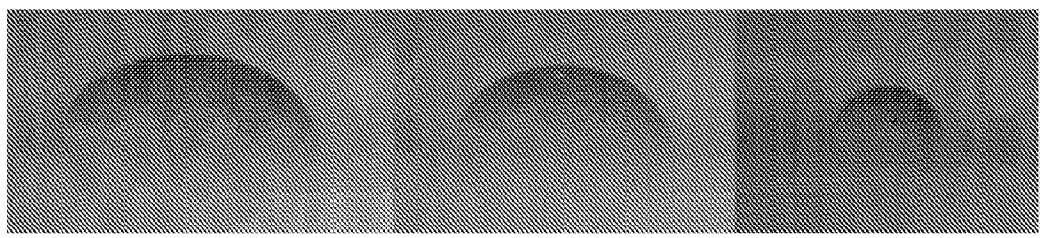
FIG. 14 shows side view images of DEX droplets on a cell monolayer immersed in the PEG phase.

Each cluster of transfected cells in the above microarrays was exposed to a 500 nl droplet containing only ~10 ng plasmid, which is significantly less than that typically used in microwell based transfections and is similar to reverse transfection protocols 8. Choosing dispensing pins with smaller volumes will reduce the size of fluorescent spots and the amount of plasmid. For example, 20 nl pins give spots of ~340 μm. Since the diameter of the DEX droplet approximately varies linearly with the square root of the drop volume, the area of transfected cell clusters can be pre-determined from the pin volume for the range of volumes studied (FIG. 1c). The resolution of circular patterns can be enhanced by using smaller volumes of the DEX phase or an ATPS system containing higher concentrations of phase-forming polymers (FIG. 13).

Example 4

Direct Cell Microprinting Using ATPS

Figure 15:
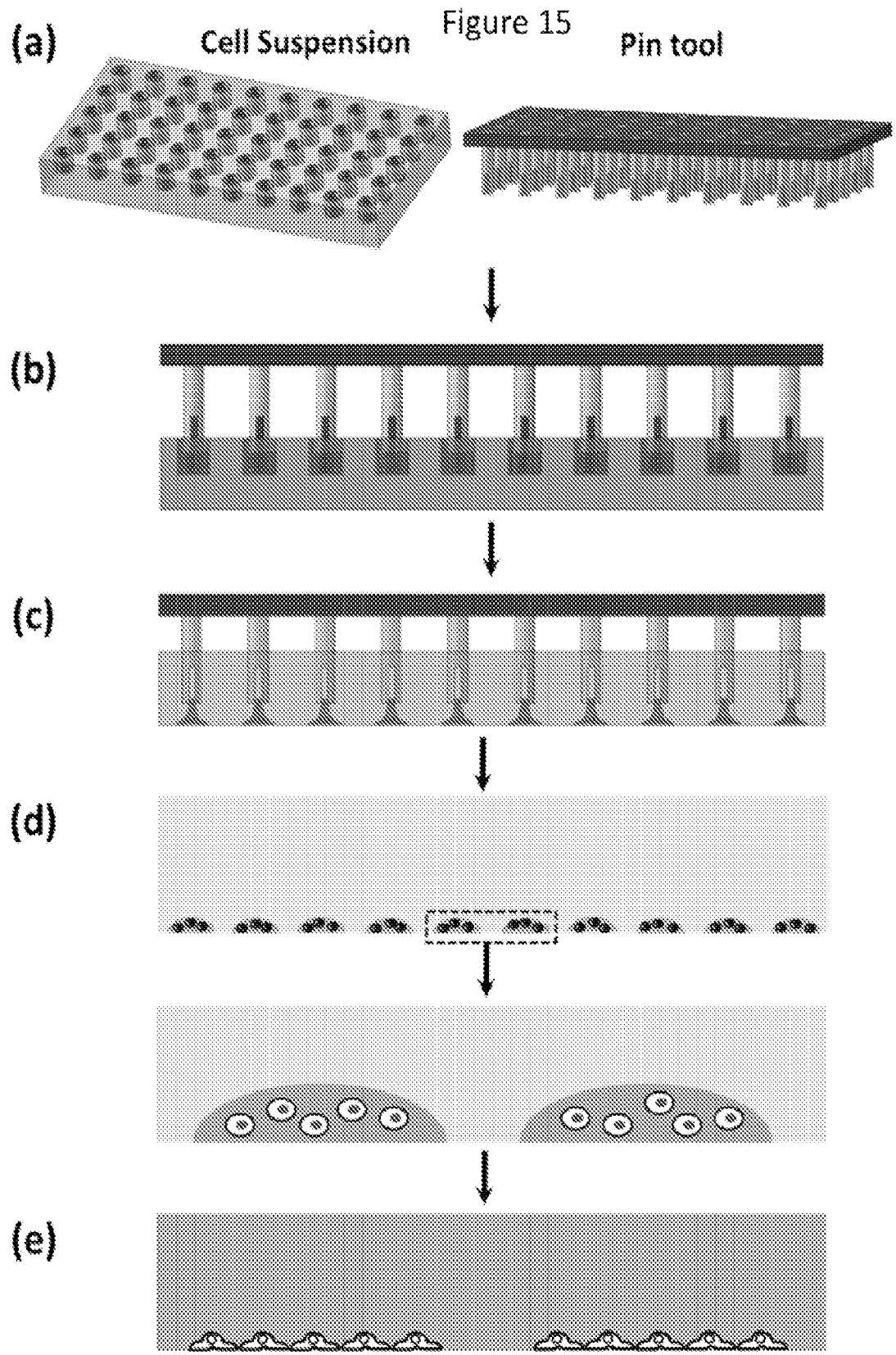
FIG. 15 shows cell printing process using two-phase technology. a. Cell suspension in the DEX phase in a 1536-well plate and the pin tool equipment, b. pins are dipped into the well plate to load with cell suspension, c. pins are lowered into a culture plate containing the PEG phase to dispense the cell suspension, d. distinct DEX droplets form on the substrate, e. after 3 hrs incubation, the two-phase media is washed and replaced by regular culture media.

Cells were directly printing cells using microliquid printing (FIG. 15). It was found that the PEG Mw:35,000/DEX Mw:500,000 pair gives an ATPS at 2.5% PEG and 3% DEX.

This system has three advantages: (i) Using lower DEX concentration eliminates the problem of delayed cell attachment and (ii) decreases the osmolality of the two-phase media, and (iii) the interfacial tension between the two aqueous phases decreases from the 4% PEG8000/5% DEX500,000 pair due to less concentrated solutions. According to the cell partition theory, this condition favours partitioning of cells to the bottom DEX phase.

Figure 16:
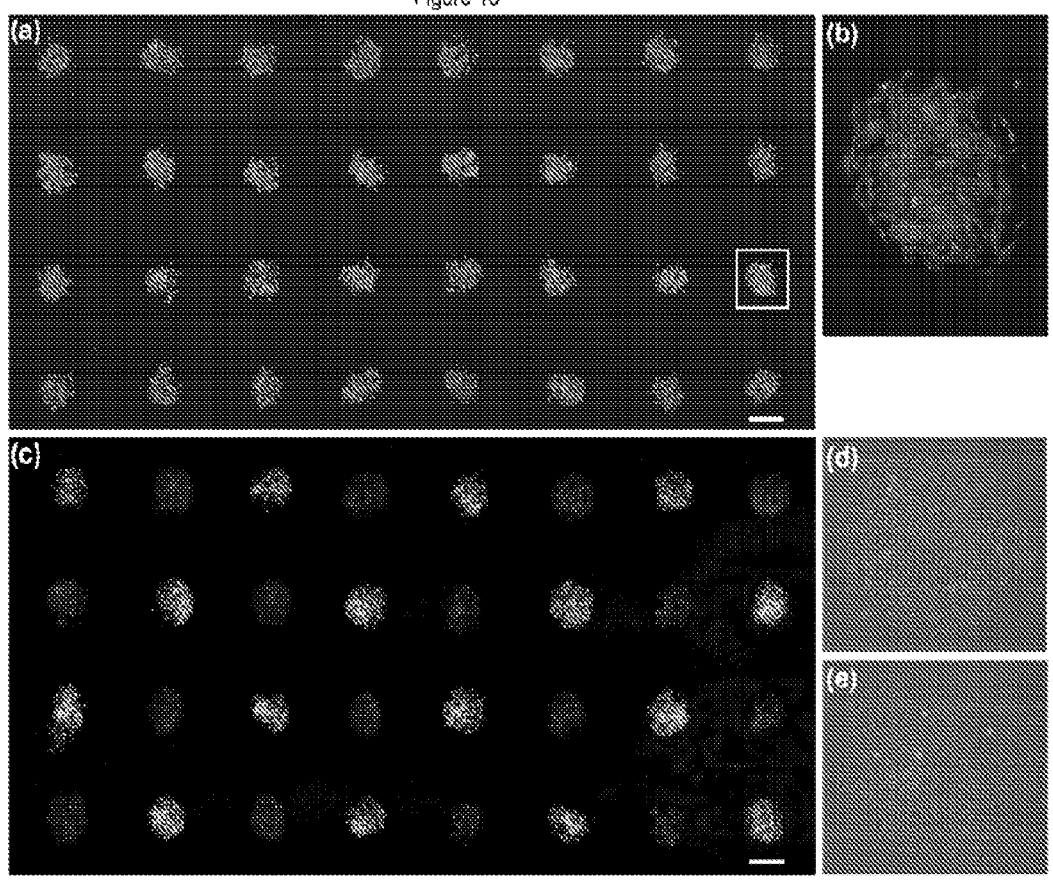
FIG. 16 shows C2C12 myoblasts printed on a culture plate. a. An 8×4 microarray of C2C12 myoblast cells stained with Calcein AM and EthD-1) post printing shows a cell viability of ~100%, b. magnified image of the boxed spot in (a), c. An 8×4 microarray of C2C12 cells stained with cell trackers and printed in an alternative format, d. magnified brightfield images of op right red and green fluorescent spots of cells in (c), scale bar 800 μm in (a) and (c).
Figure 17:
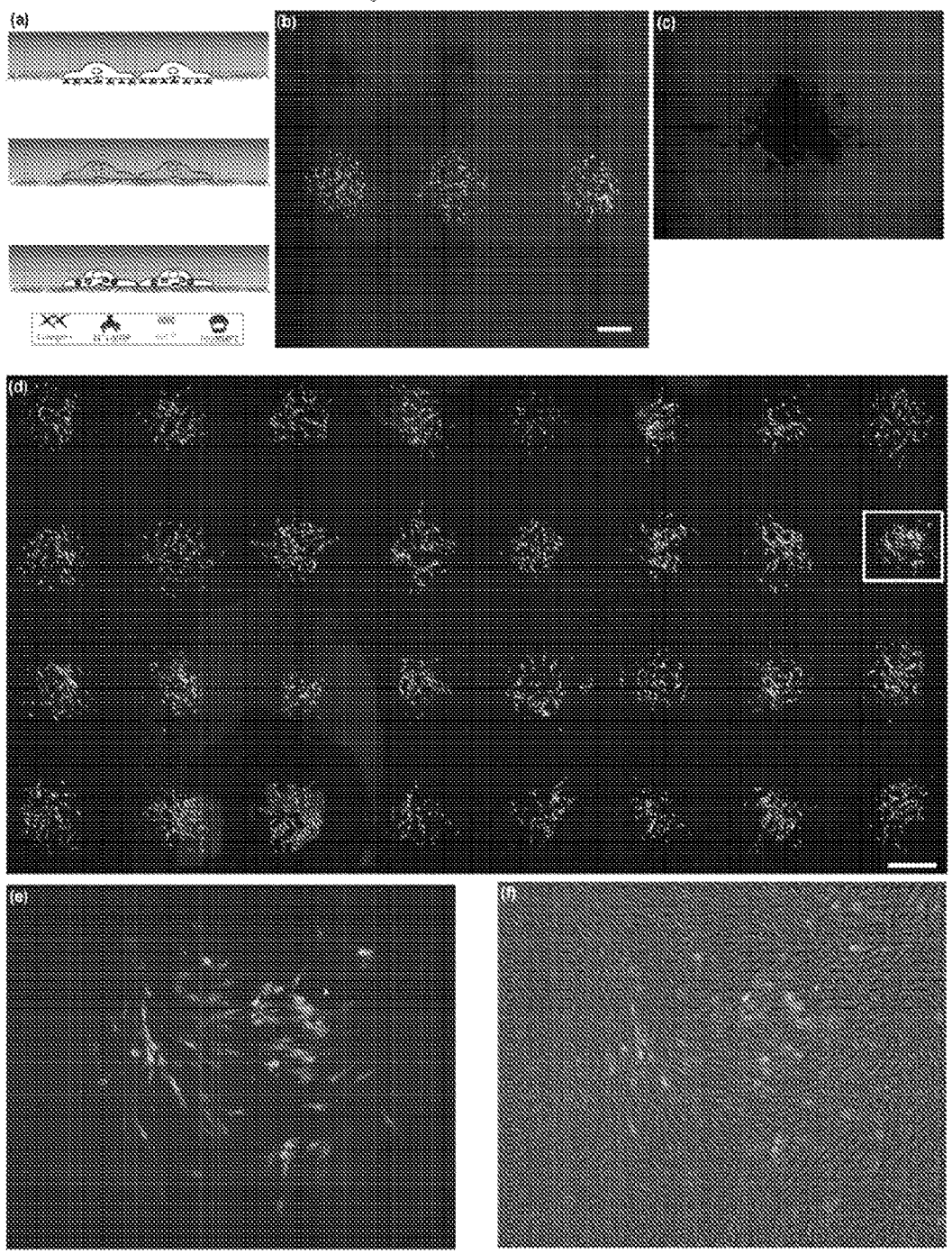
FIG. 17 shows printing cells on a monolayer of cells. a. An 8×4 microarray of C2C12 cells stained with cell tracker and printed on a monolayer of C2C12 cells stained with a different colored cell tracker, (b,c) magnified fluorescent and brightfield images of the boxed spot in (d), scale bar 500 μm in (d), 800 μm in (a).

Any cell type can be printed in pre-defined locations on solid substrates (FIG. 16) as well as soft substrates such as extracellular matrix proteins (FIG. 17a-c), cell monolayers (FIG. 17d-f), and tissues. Clean and uniform direct cell printing, however, uses a formulation different from that used for patterned gene delivery and knockdown described.

A useful aspect of clean reliable cell printing is the complete partitioning of the cells to the bottom phase (DEX phase in the case of PEG-DEX ATPS). Cells can partition to the top phase, bottom phase, localize at the interface or be distributed throughout. The patterning will not work if cells prefer the top phase or are randomly distributed throughout. Accumulation of large particulate matter such as cells at the DEX-PEG interface is a well-known phenomenon. The partition of cells in an ATPS is determined by a balance between various forces including interfacial tensions between cells and each aqueous phase ($\gamma_{1c}$ and $\gamma_{2c}$) and electrical potential between cells and the two liquid phases ($\psi_{1c}$ and $\psi_{2c}$) (FIG. 18, Eq. 1), where K represents the partition coefficient and is defined as the ratio of the number of cells in the top and bottom phases (Greson *Biochimica et Biophysica Acta*, 602, 269-280 1980). The gravitational contribution is several orders of magnitude smaller and can safely be neglected. Because both phases are made with cell culture media, their electrolyte composition similar and thus, the partition coefficient will only be determined by differences in interfacial tensions (FIG. 18 Eq. 2). Experimental determination of interfacial tensions can only be carried out if the two phases are fluid. However $\gamma_{1c}$ and $\gamma_{2c}$ involve a solid phase (cells) and cannot be measured. But Eq. 2 can be simplified using Young's Eq. 3 that relates $\gamma_{1c}$ and $\gamma_{2c}$ to interfacial tensions between the two aqueous phases $\gamma_{12}$ and contact angle, $\theta$, on a monolayer of cells of interest (FIG. 18) (Young 1804). Combining Eqs. 2 and 3 results in a linear relationship between the partition coefficient and the interfacial tensions between the two phases (FIG. 18, Eq. 4).

Eq. 4 implies that decreasing $\gamma_{12}$ will result in a smaller K value causing more cells to partition to the bottom phase. $\gamma_{12}$ itself is dependent on the concentration of phase-forming polymers and the lower polymer concentrations are used, the closer both phases to pure media and the lower the interfacial tension between them. This was tested using a new ATPS consisting of PEG Mw:35,000 and DEX Mw:500,000. This polymer pair gives ATPS at low concentrations of 2.5% PEG and 3% DEX. This formulation was used for printing cells and it was found that cells partition in favor of the DEX phase and quickly attach and spread on the substrate (within 3 hrs) and distribute uniformly within printed spots (FIG. 18). This ATPS is efficient for printing different types of cells such as C2C12 myoblasts and 231 breast cancer cells.

Ensuring Optimal Osmolality

The osmolality (tonicity) of culture media affects cell growth and morphology. Table 1 lists the osmotic pressure of representative culture media with and without DEX and PEG. Data indicates that addition of polymers increases media osmolality. In practice, osmotic pressures between 270 mOsm/kg and 340 mOsm/kg are acceptable for most cell lines. While the osmolality of the 6% DEX media is within this acceptable range, the reformulated PEG media is hypertonic and prolonged exposure of cells to it may affect cell morphology or be deleterious to cells. This is particularly important for sensitive cell types such as primary cells and stem cells.

TABLE 1

| Media | Osmolality (mOsm/kg) |
| --- | --- |
| DMEM + 10% FBS | 320 |
| Optimem | 285 |
| Optimem + 6% DEX | 299 |
| Optimem + 4% PEG | 355 |

High Throughput Cell and Reagent Micro Printing Aligner

To perform patterned delivery of reagents and cell suspensions using the ATPS technology, a series of dispensing pins with different configurations and surface properties was used. Tests showed that slot pins (design from V&P Scientific) with hydrophobic/liophobic coating perform best in terms of ease and consistency of dispensing the content. The liophobic coating prevents the liposomal complexes of nucleic acids from adhering to the interior surface of the slot.

The size of DEX droplet as a function of pin dispensing volume was evaluated. FIG. 20 shows that droplet diameter increases linearly with the square root of the pin volume. This enables the user to pre-define the desired size of the printed spot of reagents and cells. The smallest printed spot size was 340 µm obtained with a 20 nl slot pin. This size easily enables 1536 and higher density arrays.

To enable high-throughput assays and precision positioning of the 1536 and higher array of pins, the printing is done robotically. ATPS direct writing of arbitrary patterns also has a resolution of 300 µm in terms of line width and positioning.

Example 5

CXCR4 Enhances Cell Migration

To establish that CXCR4 promotes migration of breast cancer cells and illustrate limitations of standard migration assays, a wound assay, which measures nondirectional movement of cells in two-dimensional space along tissue culture substrates was used (FIG. 19). MDA-MB-231 breast cancer cells transduced with CXCR4-GFP (231-CXCR4 cells) were used (Song et al. *PLoS One* 4, e5756. 2009). CXCR4 and other chemokine receptors remain functional when fused to fluorescent proteins (van Buul et al. *J Biol Chem*, 278, 30302-30310 2003). 231-CXCR4 cells were grown to confluence in 35 mm dishes and then cultured cells overnight in medium containing 0.5% serum and then "wounded" with a 1-ml pipette tip to create a gap in the monolayer. After the wounding procedure, cells were incubated in medium containing 100 ng/ml CXCL12 or bovine serum albumin (BSA) as a negative control for 18 hours before quantifying the gap in the monolayer.

Treatment with CXCL12 significantly enhanced migration of 231-CXCR4 cells on tissue culture plastic (FIG. 19). While these data demonstrate that CXCL12-CXCR4 regulates motility of breast cancer cells, this commonly used assay cannot assess directional migration of breast cancer cells toward a chemotactic gradient.

CXCR7 Sequesters CXCL12

Two complementary approaches were used to demonstrate that CXCR7 can remove CXCL12 from the extracellular environment. First, 231 cells stably transduced with CXCR7 (Song et al. *PLoS One* 4, e5756. 2009) were incubated in medium containing 5 ng/ml of CXCL12 fused to fluorescent protein mCherry (CXCL12-cherry). CXCL12 retains full biologic activity when fused to fluorescent and bioluminescent reporter proteins (Boldajipour et al. Cell 132, 463-473 2008; Luker et al. FASEB J. 23, 823-834 2009). Within 15 minutes of incubation, 231-CXCR7 cells accumulated detectable CXCL12-cherry in intracellular vesicles, while 231-CXCR4 or control 231 cells transduced with GFP (231-GFP) did not take up the chemokine (FIG. 20). Uptake of CXCL12-cherry in 231-CXCR7 cells was blocked by CCX733, a small molecule inhibitor of CXCL12-CXCR7 binding (Luker et al. FASEB J. 23, 823-834 2009), further confirming that effects were specific to CXCR7. In these experiments, CXCL12-cherry produced in 293T cells was used. For the second approach, 231-CXCR7 or 231-GFP control cells were co-cultured with HMF that constitutively secrete CXCL12 fused to *Gaussia* luciferase (CXCL12-GL) or unfused *Gaussia* luciferase (GL) as a negative control (Luker et al. FASEB J. 23, 823-834 2009). 231-CXCR7 cells removed CXCL12-GL from the cell culture medium, reducing total amounts of chemokine in the extracellular space relative to 231-GFP cells (FIG. 22). Amounts of GL in culture medium did not differ between 231-CXCR7 or 231-GFP cells, showing specificity of CXCR7 for CXCL12 (FIG. 20). Collectively, these data establish that CXCR7 sequesters CXCL12, removing it from the extracellular environment.

Transduction of Primary Human Microvascular Endothelium with Functional CXCR7

To reproduce expression of CXCR7 on endothelial cells in tumor associated blood vessels, primary human dermal microvascular endothelial cells (HDMEC) (Lonza) were transduced with CXCR7 fused to GFP (CXCR7-GFP). These cells remove CXCL12 from the extracellular space, demonstrating that the receptor is functional.

Mutant CXCR7 does not Accumulate CXCL12

Mutations were identified in CXCR7 that abrogate accumulation of CXCL12 (FIG. 21). Mutating amino acids DRY in the second intracellular loop of CXCR7 to amino acids AAA reduces uptake of CXCL12 to background levels in control cells.

Cell Invasion Demonstration with Microliquid Printing

Figure 7:
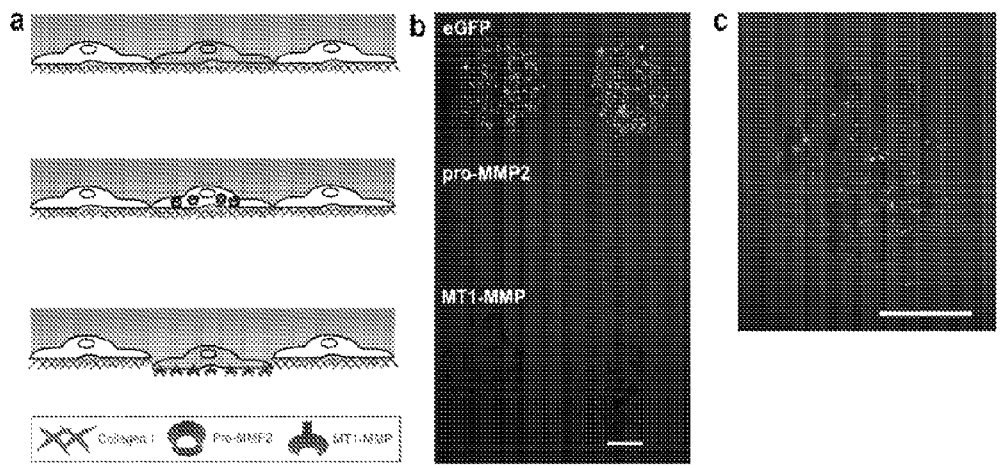
FIG. 7 shows that the solution microarray technology enables phenotypic screening of gene functions in cell cultures on physiologically-relevant substrates. a. Schematics of localized transfection of cells on collagen I surface. b. HEK293 cells cultured on collagen I and transfected with expression constructs for MT1-MMP (bottom row), MMP2 (middle row), and eGFP (top row). c. Cells were stained with antibody for MT1-MMP and imaged with a fluorescent microscope.

Patterned degradation of collagen I fibrils by matrix metalloproteinase (MMP)-expressing cells was demonstrated (FIG. 7). Recent findings highlight membrane-type1 matrix metalloproteinase (MT1-MMP) as the major regulator of the collagenolytic activity of normal and neoplastic cells (Sabeh et al., *J. Cell Biol.* 167, 769-781 2004; Hotary et al., *J. Cell Biol.* 149, 1309-1323 2000; Li et al., *Mol. Biol. Cell* 19, 3221-3233 2008). The results obtained herein are consistent with the fact that the membrane-anchored MT1-MMP undergoes intracellular processing to its active form prior to its display on the cell surface where it serves as a direct-acting collagenolysin whereas the MMP-2 zymogen is unable to degrade type I collagen directly (Li et al., 2008; supra). This experiment demonstrates the capability of microliquid printing to print on gels and to study invasion of cells through soft ECM gels such as collagen.

Example 6

Supported membranes on solids are of practical and scientific interest and allow studies such as protein-membrane interactions. To be functional, supported bilayers should remain always in an aqueous media. An optimized ATPS formulation that allows lipid printing on solid substrates in fully aqueous environments was developed. Specifically, Hydroxypropyldextran (HPD) and Dextran (DEX) phase forming polymers were used. Both phases were made in distilled water. Liposomes of interest were mixed with the DEX phase and a droplet of the resulting solution was dispensed into HPD phase over a glass slide. The two-phase system was incubated in ambient temperature for 5 min and then washed away and replaced with distilled water. A supported lipid bilayer formed on the glass slide (FIG. 22a). A second type of liposome can then be dispensed in the entire media to form a bi-colored bilayer (FIG. 22b-d). The functionality of supported bilayers was confirmed by photobleaching them using UV light (FIG. 22e) and subsequent recovery (FIG. 22f).

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in electrical engineering, optics, physics, and molecular biology or related fields are intended to be within the scope of the following claims.

We claim:

1. A system for localizing reagents, particles or cells comprising
   a) a first solution comprising a first polymer;
   b) a second solution comprising a second polymer, wherein the second solution is denser than the first solution, and wherein the first and second solutions are capable of forming an aqueous two-phase system when mixed; and
   c) a substantially flat surface of a solid or semi-solid support for the first and second solutions.

2. The system of claim 1, wherein the solid or semi-solid support further comprises a plurality of cells affixed to the support.

3. The system of claim 1, wherein the system further comprises a solution comprising a plurality of cells for printing onto the solid or semi-solid support.

4. The system of claim 1, wherein the system further comprises genetic material.

5. The system of claim 4, wherein the genetic material is selected from the group consisting of DNA, RNA, siRNA, shRNA, DNA encoding siRNA, DNA encoding shRNA, virus and phage.

6. The system of claim 1, wherein the system further comprises a test compound.

7. The system of claim 1, wherein the test compound is a drug.

8. The system of claim 1, wherein the first polymer is polyethylene glycol.

9. The system of claim 1, wherein the second polymer is dextran.

10. The system of claim 1, wherein at least one of the first solution or the second solution comprises two or more polymers.

11. The system of claim 10, wherein the two or more polymers are selected from the group consisting of dextran-methylcellulose, dextran-polyvinyl alcohol, polyethylene glycol-dextran sulfate, polyvinyl alcohol-dextran sulfate, hydroxypropyldextran-dextran, and dextran sulfate-methylcellulose.

12. The system of claim 1 further comprising a detection component configured for detection of altered cells.

13. The system of claim 12, wherein the detection component is a microscope or a fluorimeter.

14. The system of claim 1, wherein the second solution comprises at least one cell or a tissue.

15. The system of claim 1, wherein the first solution further comprises a first liposome and the second solution further comprises a second liposome, wherein the solutions are configured to a form a lipid bilayer on the support following mixing.

16. A method for localized delivery of reagents, particles or cells comprising
   a) contacting a substantially flat surface of the solid or semi-solid support with a first solution comprising a first polymer to form a coated support;
   b) contacting a portion of the coated support with a second solution comprising a second polymer and a molecule of interest under conditions whereby the first solution and the second solution are capable of forming an aqueous two-phase system when mixed;
   c) mixing the first solution and the second solution to form an aqueous two-phase system such that the portion of the coated support is contacted with the molecule of interest.

17. The method of claim 16, wherein the solid or semi-solid support further comprises a plurality of cells affixed thereto.

18. The method of claim 16, further comprising the step of printing cells onto the coated support.

19. The method of claim 17, wherein the molecule of interest is a nucleic acid and the portion of the cells is transfected with the nucleic acid.

20. The method of claim 19, wherein the nucleic acid is selected from the group consisting of DNA, RNA, siRNA, shRNA, DNA encoding siRNA, and DNA encoding shRNA.

21. The method of claim 16, wherein the molecule of interest is a virus or a phage.

22. The method of claim 16, wherein the molecule of interest is a test compound.

23. The method of claim 22, wherein the test compound is a drug.

24. The method of claim 16, wherein the molecule of interest is a cell or a tissue.

25. The method of claim 16, wherein the first polymer is polyethylene glycol.

26. The method of claim 16, wherein the second polymer is dextran.

27. The method of claim 16, wherein at least one of the first solution or the second solution comprises two or more polymers.

28. The method of claim 27, wherein the two or more polymers are selected from the group consisting of dextran-methylcellulose, dextran-polyvinyl alcohol, polyethylene glycol-dextran sulfate, polyvinyl alcohol-dextran sulfate, hydroxypropyldextran-dextran, and dextran sulfate-methylcellulose.

29. The method of claim 17, further comprising the step of detecting alterations in the cells contacted with the second solution and the molecule of interest.

30. The method of claim 29, wherein the alterations are selected from the group consisting of transfection of nucleic acids, infection with virus or phage, and alterations of cellular signaling molecules.

31. The method of claim 16, wherein the first solution further comprises a first liposome and the second solution further comprises a second liposome, wherein the solutions are configured to form a lipid bilayer on the support when mixed.

* * * * *